United States Patent
Koo et al.

[11] Patent Number: 5,849,642
[45] Date of Patent: Dec. 15, 1998

[54] METHOD OF FABRICATING SPECIMEN FOR EXPOSING DEFECTS OF A SEMICONDUCTOR DEVICE FOR OBSERVATION AND ANALYSIS

[75] Inventors: Jeong-Hoi Koo, Seoul; Doo-Jin Park, Onyang, both of Rep. of Korea

[73] Assignee: Hyundai Electronics Industries Co., Ltd., Kyoungki-do, Rep. of Korea

[21] Appl. No.: 684,454

[22] Filed: Jul. 19, 1996

[30] Foreign Application Priority Data

Jul. 19, 1995 [KR] Rep. of Korea .................. 95-21183

[51] Int. Cl.⁶ .......................... B44C 1/22; C03C 15/00
[52] U.S. Cl. ........................ 438/745; 216/83; 216/84
[58] Field of Search .................... 438/745; 216/83, 216/84

[56] References Cited

U.S. PATENT DOCUMENTS

| | | | |
|---|---|---|---|
| 3,724,066 | 4/1973 | Wainer et al. ................ | 216/84 X |
| 4,094,752 | 6/1978 | Vahe ............................. | 438/745 X |
| 5,131,752 | 7/1992 | Yu et al. ....................... | 356/369 |
| 5,191,213 | 3/1993 | Ahmed et al. ................ | 250/310 |
| 5,214,283 | 5/1993 | Le ................................ | 250/307 |
| 5,498,871 | 3/1996 | Koo et al. ..................... | 250/307 |

OTHER PUBLICATIONS

IBM Technical Disclosure Bulletin, vol. 21, No. 2, "Measuring Boron Duping Profiles in Silicon", Briska,. p. 671, Jul. 1978.

*Primary Examiner*—Bernard P. Codd
*Attorney, Agent, or Firm*—Ware, Fressola, Van Der Sluys & Adolphson LLP

[57] ABSTRACT

A method of fabricating a specimen for the observation and analysis of defects in a wafer includes the steps of: locating a position of a defect which exists in a patterned layer of a wafer on which a semiconductor device is formed; forming a photoresist layer on an outer side of the patterned layer at the position; drilling the wafer to form a hole from an underlying, outer portion of the wafer to the outer side, i.e., a top portion of the patterned layer where the diameter of the hole formed gradually decreases from the underlying portion to the top portion; and etching the drilled portion to remove the remaining residue.

8 Claims, 4 Drawing Sheets

1

METHOD OF FABRICATING SPECIMEN FOR EXPOSING DEFECTS OF A SEMICONDUCTOR DEVICE FOR OBSERVATION AND ANALYSIS

CROSS REFERENCE TO RELATED APPLICATIONS

Reference is made to co-owned, copending U.S. patent applications Ser. No. 08/684,451 entitled, "Method of Fabricating Specimen for Analyzing Defects of Semiconductor Device", and Ser. No. 08/684,453 entitled, "Method of Analysing Defects of Semiconductor Device with Three Dimensions", filed on even date herewith and which are hereby incorporated by reference.

FIELD OF THE INVENTION

The present invention relates, in general, to a method of fabricating or preparing a specimen for exposing the defects of a semiconductor for observation and analysis.

DESCRIPTION OF THE PRIOR ART

As a semiconductor device is highly integrated, each layer of a semiconductor device has been changed to a complicated structure of a three dimensional array so as to maximize the storage capacity. Accordingly, observation from various perspectives is required to detect any defects existing in the patterned layers of a wafer.

After identifying a defect with a bit map test, the methods for observing defects of the patterned layer formed on the substrate in a multi-structured semiconductor device, top and oblique views are used to observe the defects from the formed upper layer to the lower layer. Through the above-mentioned methods, however, there are instances where it is impossible to analyze the defects such as in the case of an open contact or misalignment. Therefore, in order to solve this problem, there has been proposed a method of backside etching which grinds and then etches the backside of substrate until the patterned layer is exposed. In this method, polishing of backside of the substrate is done mechanically and then processing of the polished surface is done chemically, resulting in the exposure of the defective pattern.

Referring to FIGS. 1A to 1C, the backside etching technology according to an embodiment of the conventional art is described.

First, as shown in FIG. 1A, an outer side of the patterned layer 2 formed on a silicon substrate 1 is molded, with a protective resin resulting in a molded layer 3. Hereinbelow, all of the substrate 1, the patterned layer 2 and the molded layer 3 is referred to as a first specimen 6. Afterwards, as shown in FIG. 1B, the specimen 6 is set over a rotating plate 4 of the polisher with an outer side of the molded layer 3 facing upward and held in a fixed position with respect to the rotatable plate 4. After the setting process, the an outer side of substrate 1 starts to be polished by rotation of the rotatable plate 4 and the polishing process is continued until the substrate 1 is almost removed and an inner side of the patterned layer 2 at the substrate/patterned layer interface is almost exposed. Afterwards, substrate residue which remains after the polishing process is removed by a the mixed solution of $HNO_3$ and HF. Through the above process, a second specimen 7 for the observation of a defective layer is obtained a s shown in FIG. 1C.

The conventional method of preparing a specimen for the observation of defects, however, has problems in that the exposed region of the pattern is irregular and very narrow. Therefore, it is impossible to detect the position of a the defective pattern exactly and to designate the end point at which the inner side of the patterned—therefor; layer starts to be exposed. Resultantly, the conventional method has a problem of a high failure rate for fabricating the specimen for the analysis.

In addition, there is also a problem in that it takes much time for fabrication of the specimen because the silicon substrate 1 is wholly polished to expose the formed patterned layer. Moreover, as shown in FIG. 1C, the residue 5 of the silicon substrate 1 remains on the surface of the inner side of the patterned layer because of the irregular polishing rate of the polisher. The result is that the exposed patterns are irregular despite the fact that wet etching is completed. In other words, the exposed patterns do not appear in constant positions but, as is shown in FIG. 1C, here and there. Accordingly, it is impossible to trace the positions of failures.

In addition to the above-mentioned problems, the conventional method has to divide the wafer having defects with dies, so as to analyze the defect. That is, the method has a problem that it is impossible to analyze only the portion having defects without dividing the wafer into dies.

SUMMARY OF THE INVENTION

Accordingly, the object of the present invention is to provide a method of fabricating a specimen for analyzing the defects of a semiconductor which makes it possible to analyze the portion having defects without dividing the corresponding die having defects from a wafer state.

According to the present invention, a method of fabricating a specimen for analyzing the defects of a semiconductor comprises the steps of: searching for and locating a position having a defect in a patterned layer of a wafer on which a semiconductor device is formed; forming a photoresist layer at said position on the patterned layer; drilling a portion of said wafer to form a drilled portion hole from an outer side, i.e, an underlying portion of a substrate layer of the wafer to a top portion, i.e., an outer side of the patterned layer wherein a diameter of the hole formed, i.e., the drilled portion gradually decreases from said outer side of the substrate layer to said outer side of said patterned layer; and etching the drilled portion to remove the a remaining residue, thereby exposing the defect for observation and analysis.

BRIEF DESCRIPTION OF THE DRAWINGS

These and other features, aspects, and advantages of the present invention will become better understood with regard to the following description, appended claims, and accompanying drawings wherein:

DETAILED DESCRIPTION OF THE INVENTION

Hereinbelow, the preferred embodiment of the present invention is described in detail.

Figure 1A:
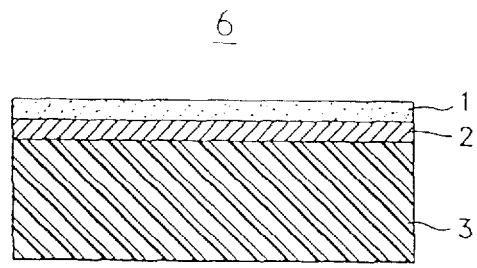
FIGS. 1A to 1C are a method of fabricating a specimen for the analysis of defects in a wafer according to the conventional art.
Figure 1B:
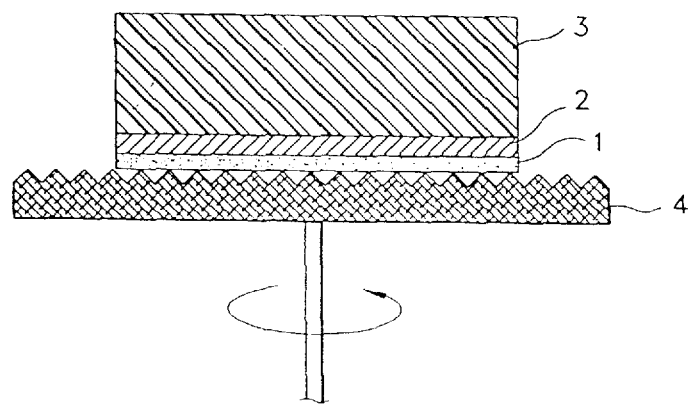
Figure 1C:
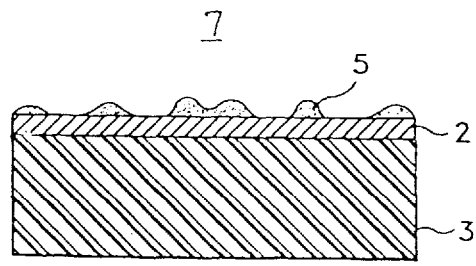
Figure 2A:
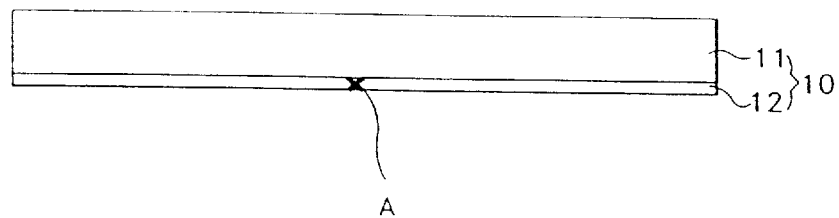
FIGS. 2A to 2C are a method of fabricating a specimen for the analysis of defects in a wafer according to an embodiment of the present invention.
Figure 2B:
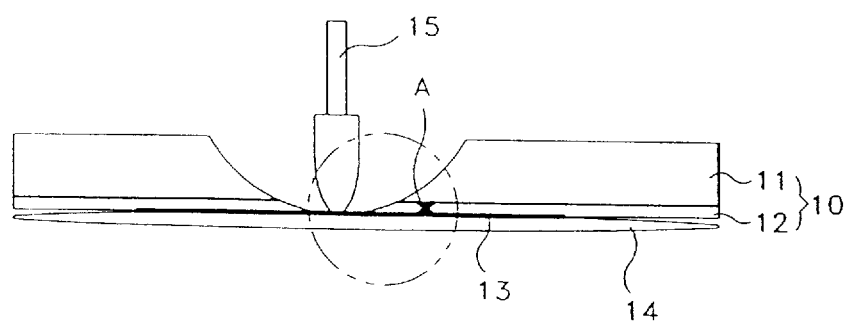
Figure 2C:
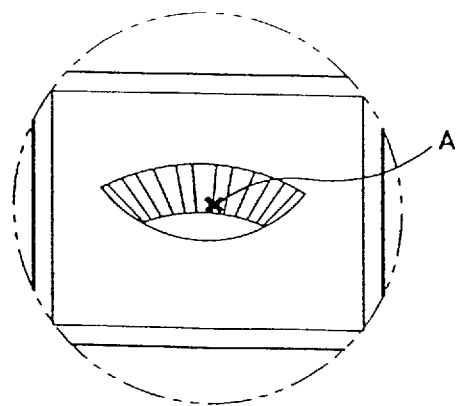

FIG. 2A to 2C are a method of fabricating a sample for the analysis of defects in a wafer according to an embodiment of the present invention.

Referring to FIG. 2A, a wafer 10 having a patterned layer 12 formed on a silicon substrate layer 11 is shown an outer side of the substrate layer is shown at the top and an outer side of the patterned layer is shown at the bottom in FIG. 2A. An interface between the substrate layer and the patterned layer is formed by facing inner sides of the substrate and patterned layers. Point A in the figure indicates the position where a failure has been found to exist in the patterned layer 12.

Now referring to FIG. 2B, first, a die in which a failure occurred, is searched for and located in a first step and the wafer including the die is coated by photoresist film 13. Afterwards, a clean paper or soft cloth 14 is put on a plate for a drilling step and then the wafer is put thereon in the manner shown. The soft cloth or clean paper is to prevent an affect due to the weight of the wafer itself and the weight caused by pressing upon drilling.

In a second step, the wafer is fixed on the plate for the drilling and then the an outer side i.e., the backside of the substrate layer of wafer is drilled with centering thereof at a point adjacent to the position A where a failure occurs, using a drill 15 until a hole or drilled portion is formed in the wafer 10 by the drilling.

The drilled portion is formed by drilling the wafer from an outer side of the substrate layer of the wafer, i.e., the underlying portion to an outer side of the patterned layer, i.e, the top thereof, so that a diameter of the hole or drilled portion formed, gradually decreases from said outer side of the substrate layer of the wafer to the outer side of the patterned layer.

Since the thickness of a drilled face around the so formed drilled portion is thin, the failure position A can be detected from the inside of a thin tilted region thereof that is indicated within the circle of FIG. 2B as shown in detail in FIG. 2C.

The third step is to expose the failure pattern by using chemicals. At this time, the exposure of the pattern starts from the edge of the drilled portion forming the thin hole. In order to prevent the patterned layer from being drilled too much, i.e., so as to prevent drilling the position of the failure, it is important to designate the end-point. The designation of the end-point is easily performed from the top view of the face from which the drilling is progressed, via optical microscopy.

Two kinds of etching chemicals are used to expose the patterned layer in the present invention.

One is a dilute solution of KOH which roughly etches the drilled wafer and the other is a mixed solution of HF+HNO$_3$+CH$_3$COOOH which finely etches the roughly etched wafer. The latter solution is able to expose the patterned layer without damaging the pattern.

For the above-mentioned solution of KOH, the reaction occurs only at the drilled portion. Therefore, a portion not to be ground, is not etched. When only the solution of KOH, however, is used to expose the patterned layer, the pattern is damaged by the solution of KOH because of overetching due to the solution's high etching rate.

Accordingly, after the rough etching by the solution of KOH, the mixed solution of HF+HNO$_3$+CH$_3$COOH is used for the last processing step of the etching to expose the pattern without damage.

It is preferred to etch the ground face through the two etching steps using the above solutions. Also, it is possible to use the solution of dilute KOH for rough etching and to use an appropriate solution for fine etching. Moreover, it is possible to use an appropriate solution for rough etching and to use the mixed solution of HF+HNO$_3$+CH$_3$COOH for fine etching.

Figure 3:
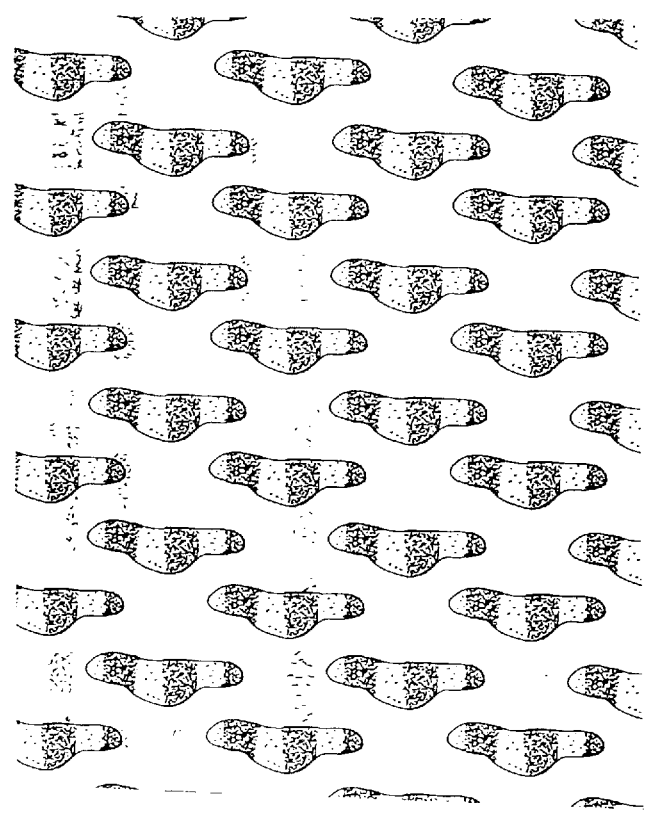
FIG. 3 is an illustrative view of the specimen fabricated according to the method of FIGS. 2A to 2C.
Figure 4:
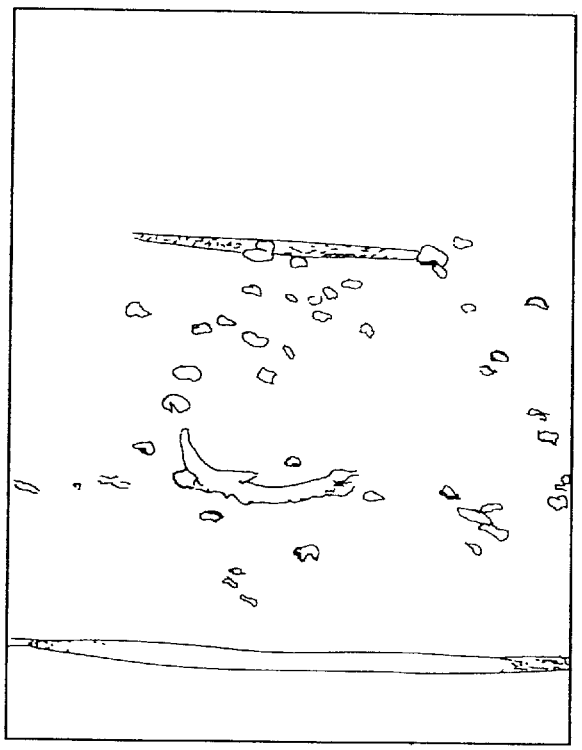
FIG. 4 is an illustrative view of the metal contact portion in FIG. 3.

Scanning electron microscopy(SEM) photographs for the analysis of the defects are obtained after the fabricated specimens are respectively loaded to SEM apparatus. Although such photographs are not available, FIG. 3 is a drawing showing what would be shown in such a photograph, i.e., a misalignment in unit cells of DRAM which is formed in the ground region. Similarly, FIG. 4 is a drawing showing contact voids that occurred in the metal contact of an arbitrary cell.

In FIG. 3, each V-shaped pattern is a unit cell having one transistor and one capacitor. From FIG. 3, it is determined that, while the metal contact process was performed, misalignment occurred at the contact portion. FIG. 4 shows voids generated at the contact area by misalignment or for some other reason and are indicated by the irregularly shaped points.

Meanwhile, before observing after loading the specimen for the analyeis to the scanning electron microscope, in order to prevent the specimen for the analysis from being charged-up, other portions of backside except the exposed portion of the defect are covered with aluminum foil. On covering with the aluminum foil, the photoresist film is not removed to protect the pattern. Afterwards, the photoresist film is removed by a solution of acetone. Lastly, a cleaning process is performed.

As described hereinbefore, in the case that the analysis and observation is performed only by a top view or an oblique view method, there may be instances where it is impossible to analyze the defects. For example, one is unable to observe the state of the bottom face or inner side of the pattern. In another case, when the wafer is divided into each die to analyze the specific defect, one is unable to analyze the mechanism of the defects statistically.

On the other hand, when the present invention is applied, it is possible to observe the defect generated in the bottom face. In addition, since the wafer is not divided to analyze the defect, it makes it possible to analyze the defect generated in one wafer statistically. Moreover, since the invention may again use the remaining dies except the die used for the analysis, material cost is decreased.

Although the preferred embodiment of the present invention has been disclosed for illustrative purposes, those skilled in the art will appreciate that various modifications, additions and substitutions are possible, without departing from the scope and spirit of the present invention as disclosed in the accompanying claims.

What is claimed is:

1. A method of fabricating a specimen for analyzing defects in a patterned layer of a semiconductor wafer having said patterned layer formed on a silicon substrate at an interface between facing inner sides of the substrate and the patterned layer, comprising the steps of:

locating a position having a defect in the patterned layer of the wafer on which a semiconductor device is formed;

forming a photoresist layer on an outer side of the patterned layer parallel to said facing inner sides at said position;

drilling a portion of said wafer to form a drilled portion from an outer side of the substrate parallel to said facing inner sides to the outer side of the patterned layer wherein a diameter of the drilled portion gradually decreases from said outer side of the substrate layer to said outer side of said patterned layer; and etching the drilled portion to remove a remaining residue thereby exposing the defect for observation.

2. The method according to claim 1, wherein said drilling step starts from the outer side of the substrate of the wafer after a soft member is put on a plate for the drilling step and then said wafer is set on the soft member.

3. The method according to claim 1, wherein a starting position of the drilling step is a predetermined position adjacent to the defective position.

4. The method according to claim 1, wherein said etching step comprises a rough etching step and a fine etching step.

5. The method according to claim 4, wherein a solution for said rough etching is a solution of dilute KOH.

6. The method according to claim 4, wherein a solution for said fine etching is a mixed solution composed of HF, $HNO_3$ and $CH_3COOH$.

7. The method according to claim 4, wherein a solution for said rough etching is a solution of dilute KOH and a solution for said fine etching is a mixed solution composed of HF, $HNO_3$ and $CH_3COOH$.

8. A method of fabricating a specimen for analyzing the defects in a patterned layer of a semiconductor wafer having said patterned layer formed on a silicon substrate at an interface between facing inner sides of the substrate and the patterned layer, comprising the steps of:

locating a position having a defect in a patterned layer of a wafer on which a semiconductor device is formed;

forming a photoresist layer on an outer side of the patterned layer parallel to said facing inner sides at said position;

drilling a portion of said wafer to form a drilled portion from an outer side of the substrate parallel to said facing inner sides to the outer side of the patterned layer wherein a diameter of the drilled portion gradually decreases from said outer side of the substrate layer to said outer side of said patterned layer;

etching the drilled portion to remove a remaining residue;

covering other portions of the wafer except the defective portion with aluminum foil; and removing the photoresist layer thereby exposing the defect for observation.

\* \* \* \* \*

UNITED STATES PATENT AND TRADEMARK OFFICE
CERTIFICATE OF CORRECTION

PATENT NO. : 5,849,642
DATED : December 15, 1998
INVENTOR(S) : Jeong-Hoi Koo, Doo-Jin Park It is certified that error appears in the above-indentified patent and that said Letters Patent is hereby corrected as shown below:

ON THE TITLE PAGE:

At INID [57], line 7 of the Abstract, after "i.e.," insert --to--.

At column 1, line 62, cancel "the".

At column 1, line 65, cancel "a s" and substitute --as-- therefor.

At column 2, line 2, cancel "the" (second occurrence).

At column 2, line 4, cancel "-therefor;".

At column 2, line 17, cancel "is".

At column 2, line 37, prior to "hole", insert --or--.

UNITED STATES PATENT AND TRADEMARK OFFICE
CERTIFICATE OF CORRECTION

PATENT NO. : 5,849,642
DATED : December 15, 1998
INVENTOR(S) : Jeong-Hoi Koo, Doo-Jin Park It is certified that error appears in the above-indentified patent and that said Letters Patent is hereby corrected as shown below:

At column 2, line 43, cancel "the" (second occurrence).

At column 3, line 22, cancel "the" (first occurrence).

At column 3, line 22, after "outer side", insert --,--.

At column 3, line 23, after "of", insert --the--.

At column 3, line 34, cancel "so formed" and substitute --so-formed-- therefor.

At column 4, line 23, cancel "analyeis" and substitute --analysis-- therefor.

Signed and Sealed this

Second Day of November, 1999

Q. TODD DICKINSON

Attest:

Attesting Officer

Acting Commissioner of Patents and Trademarks